United States Patent
Baudino

[19]

[11] Patent Number: 6,139,539
[45] Date of Patent: *Oct. 31, 2000

[54] MICROBORE CATHETER WITH VELOCITY REDUCING CHAMBER

[75] Inventor: Michael D. Baudino, Coon Rapids, Minn.

[73] Assignee: Medtronic, Inc., Minneapolis, Minn.

[*] Notice: This patent is subject to a terminal disclaimer.

[21] Appl. No.: 09/170,019

[22] Filed: Oct. 13, 1998

Related U.S. Application Data

[63] Continuation-in-part of application No. 08/641,185, Apr. 30, 1996, Pat. No. 5,820,610.

[51] Int. Cl.$^7$ .................................................. A61M 25/00
[52] U.S. Cl. ........................ 604/537; 604/264; 604/523
[58] Field of Search .................................. 604/264, 523, 604/534, 27

[56] References Cited

U.S. PATENT DOCUMENTS

| | | | |
|---|---|---|---|
| 4,373,527 | 2/1983 | Fischell | 128/260 |
| 4,681,560 | 7/1987 | Schulte et al. | 604/9 |
| 4,692,147 | 9/1987 | Duggan | 604/93 |
| 5,045,060 | 9/1991 | Melsky et al. | 604/93 |
| 5,137,529 | 8/1992 | Watson et al. | 604/891.1 |
| 5,207,650 | 5/1993 | Martin | 604/173 |
| 5,356,381 | 10/1994 | Ensminger et al. | 604/93 |
| 5,399,168 | 3/1995 | Wadsworth, Jr. et al. | 604/175 |
| 5,460,618 | 10/1995 | Harreld | 604/264 |
| 5,503,630 | 4/1996 | Ensminger et al. | 604/93 |
| 5,637,102 | 6/1997 | Tolkoff et al. | 604/283 |
| 5,820,610 | 10/1998 | Baudino | 604/280 |

*Primary Examiner*—Wynn Wood Coggins
*Assistant Examiner*—Jennifer Maynard
*Attorney, Agent, or Firm*—Howrey Simon Arnold & White, LLP

[57] ABSTRACT

A catheter having minimal dead volume due to a "micro" or very small internal diameter for the majority of its length. The distal tip of the catheter, which is the end disposed within the body proximate the location at which the pharmaceutical agent or other fluids are to be delivered, includes a chamber, compartment or other relatively wider internal diameter section, so that the internal diameter rapidly expands in the transitional region between the proximal portion of the catheter (with the very small or micro internal diameter) and the distal portion of the catheter (which includes the catheter tip). The expanding internal diameter causes the velocity of fluid being delivered to decrease prior to its ejection through a distal opening. Also disclosed is a fluid delivery system comprising a stylet lumen separate from a delivery lumen. Separate stylet and delivery lumens permit these different portions of the catheter to be independently constructed to maximize the suitability of each lumen for its intended purpose. The catheter of the present invention may be employed within fully implantable or partially implantable applications depending upon the type of fluid supply device used to introduce fluids into the catheter for delivery to the distal tip disposed at the fluid ejection site.

24 Claims, 2 Drawing Sheets

6,139,539

MICROBORE CATHETER WITH VELOCITY REDUCING CHAMBER

CROSS-REFERENCE TO RELATED APPLICATION

This application is a continuation-in-part of U.S. patent application Ser. No. 08/641,185, filed Apr. 30, 1996, now U.S. Pat. No. 5,820,610.

BACKGROUND OF THE INVENTION

I. Field of the Invention

The present invention relates generally to an assembly for delivering fluids to a desired location within the body; and more particularly, relates to a catheter or similar medical device used to infuse pharmaceutical agents or other fluids into the body so that the velocity of the stream of injected fluid at or near the fluid ejection or delivery site is reduced so as to avoid unintended injury or trauma to body tissues from the fluid ejection.

II. Discussion of the Prior Art

Physicians today often use a microbore catheter placed to extend to a selected location within a patient's body for both the administration and receipt of fluids. Microbore catheters are catheters which generally have a very small internal diameter along their lengths. Microbore catheters have a unique advantage over other conventional catheters in that they tend to be more slender, making them easier to use. Ease of use is particularly advantageous when catheters are utilized for various neurological applications. For instance, placement of a parenchymal catheter near or within the brain for all practical purposes requires that a relatively small device like a microbore catheter be used to avoid unintended injury to the brain. (Use of a parenchymal catheter generally involves the insertion of a catheter within the brain to dispense pharmaceutical agents at a specific desired location; the locations include the ventricular spaces of the brain.)

It is also generally advantageous for catheters to have a relatively smaller internal diameter since a smaller internal diameter results in the catheter having reduced dead volume. Dead volume is equivalent to the total carrying capacity of the catheter at any given time. The larger the carrying capacity the more fluid must flow into the catheter before being available for delivery to a site within the patient's body. Thus, minimizing dead volume is important in situations where very low flows are required to limit delay in delivery of the fluid to the desired site and in limiting bolusing of small dosages of drugs.

Using conventional microbore catheters to deliver pharmaceutical agents or other fluids to a desired location within the body, however, has a significant drawback. While the use of small size catheters can be an advantage on one hand, the use of microbore catheters also can be disadvantageous precisely because of their small size. More specifically, the small inner diameter of the microbore catheter causes the fluid to be delivered at a relatively high velocity, particularly when the fluid is being supplied to the catheter by manual means, such as a syringe, or by a drug infusion pump (external or implantable) programmed to provide bolus injections. The high velocity achieved by shooting the fluid through the narrow lumen of the catheter can create a harmful cutting or otherwise traumatizing injury to tissues adjacent the microbore catheter at the fluid ejection site.

SUMMARY OF THE INVENTION

As explained in more detail below, the present invention overcomes the above-noted and other shortcomings of prior microbore catheters and methods.

The present invention preferably comprises a catheter that has minimal dead volume due to a "micro" or very small internal diameter for the majority of its length. In addition, however, the distal tip of the catheter, which is the end disposed within the body proximate the location at which the pharmaceutical agent or other fluids are to be delivered, includes a chamber, compartment or other relatively wider internal diameter section, so that the internal diameter rapidly expands in the transitional region between the proximal portion of the catheter (with the very small or micro internal diameter) and the distal portion of the catheter (which includes the catheter tip). The expanding internal diameter causes the velocity of fluid being delivered to decrease prior to its ejection through a side or end hole, slit valve, or other such opening, as shown generally in FIG. 1.

In an alternate embodiment, shown generally in FIG. 3, the fluid delivery assembly of the present invention comprises a stylet lumen separate from a delivery lumen. Separate stylet and delivery lumens permit these different portions of the catheter to be independently constructed to maximize the suitability of each lumen for its intended purpose. For example, the narrow delivery lumen of the microbore catheter can be made in accordance with the present invention without any alteration in the design and construction of the stylet lumen.

The foregoing features of the present invention have been broadly outlined in order that the detailed description that follows may be understood and so that contributions which the invention provides to the art may be better appreciated. The invention is described in greater detail below, with additional features being set forth with reference to the figures provided and included within the subject matter of the claims appended hereto.

DETAILED DESCRIPTION OF THE INVENTION

Figure 1:
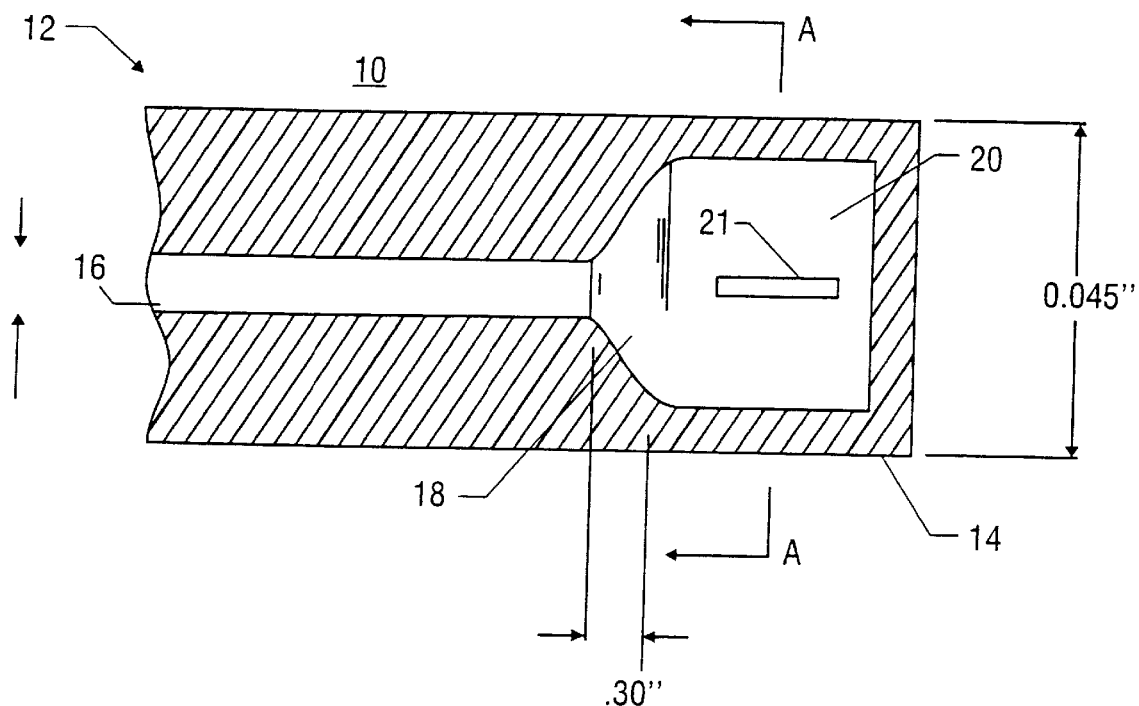
FIG. 1 is an illustration of the distal end of a closed tip configuration of an exemplary microbore catheter in accordance with the present invention, depicted in vertical section.

Referring initially to FIG. 1, shown is a microbore catheter 10 provided in accordance with a first preferred embodiment of the present invention. The catheter 10 generally comprises an elongated tubular member for delivering fluid to an ejection site within a living body. The catheter 10 includes a proximal end 12 and a distal end 14, wherein the distal end 14 is disposed at a predetermined fluid ejection site within the body and the proximal end 12 receives fluid from a fluid supply device (not shown) for delivery to the distal end 14. The catheter 10 of the present invention may be fully implantable or partially implantable depending upon the application. In a fully implantable catheter application, both the proximal end 12 and distal end 14 are implanted within the body, with the proximal end 12 coupled to any of a variety of well known implantable fluid supply devices (not shown), including but not limited to an implantable catheter access port, illustrative examples of which are disclosed in U.S. Pat. Nos. 5,137,529, 4,681,560, 5,045,060, 5,399,168, 5,503,630, and 5,637,102, or an implantable drug infusion pump, illustrative examples of which are disclosed in U.S. Pat. Nos. 4,692,147 and 4,373,527, the teachings of which are hereby incorporated by reference. In a partially implantable catheter application, the proximal end 12 is located outside of the body for connection to any of a variety of well known external fluid supply devices (not shown), including but not limited to an external drug infusion pump or a manual apparatus for introducing fluids into the proximal end 12, such as a syringe assembly.

Fluid introduced at proximal end 12 travels through a first lumen portion 16 of catheter 10, having a relatively small diameter. Fluid travels through first lumen portion 16 to distal end 14 of catheter 10 within which first lumen portion 16 continues, defining a continuous fluid passageway, and then terminates. The inner diameter of first lumen portion 16 generally will be approximately 0.015 inches throughout, consistent with the internal diameter dimensions for a microbore catheter.

First lumen portion 16 terminates in distal end 14 at a transition lumen portion 18 with which first lumen portion is in direct fluid communication to continue the fluid passageway of first portion 16. Transition lumen portion 18 begins at the termination point of first lumen portion 16 with an internal diameter identical to that of first internal portion 16. The internal diameter of transition lumen portion 18 then undergoes relatively rapid expansion of its internal diameter from the point at which it meets first lumen portion 16 along its length within distal end 14 to a point at which it meets a second lumen portion 20 having a relatively wide internal diameter.

The internal diameter of transition lumen portion 18 generally will be approximately 0.045 inches at its distal most end, about equal to the internal diameter of lumen portion 20. The expansion of the internal diameter of transition lumen portion 18 of catheter 10 from the internal diameter of first lumen portion 16 to its expanded internal diameter at its distal-most point generally will be achieved over a relatively short length of about 0.30 inches. This preferred length represents a ratio of 20 to 1 in comparison with the internal diameter of first lumen portion 16.

Transition lumen portion 18 terminates at second lumen portion 20 with which it is fluid communication such that second lumen portion 20 comprises a continuation of the fluid passageway of the first lumen portion 16 and transition lumen portion 18. Second lumen portion 20 is at the distal most portion of distal end 14 of catheter 10, which as shown in FIG. 1 may be a closed end.

The internal diameter of second lumen portion 20 may be the same throughout its length, or it may vary (e.g., be tapered) depending upon the application. That is, it may or may not have the same internal diameter as at the point it meets transition lumen portion 18. Furthermore, in at least one preferred embodiment, ejection of catheter fluid may take place through a side slit 21 as shown in FIG. 1. Alternatively, distal end 14 may contain a second lumen portion 20 with an end hole, a slit valve or another type aperture or exit opening for fluid ejection (see FIG. 3).

Regardless of the particular apparatus and resulting manner for ejection of delivered fluid, in view of the foregoing described construction of catheter 10, the delivered fluid will be slowed before its ejection from second lumen portion 20 to prevent tissue trauma due to overly rapid ejection. The relative velocity of the fluid to be delivered in second lumen portion 20 (in comparison to its travel velocity in first lumen portion 16) is directly proportional to the ratio of the cross-sectional area of the first and second lumen portions, 16 and 20. Thus, by making the internal diameter of second lumen portion 20 larger than the internal diameter of first lumen portion 16, the velocity of fluid in second lumen portion 20 decreases in comparison with the fluid speed through first lumen portion 16.

Rapid fluid speed and relative narrowness are desirable for moving a reduced amount of dead volume fluid through first lumen portion 16 to transition lumen portion 18 quickly. Thereafter, however, dead volume is increased in only a limited way by the relative short portion of catheter 10 comprising second lumen portion 20 in distal end 14. The reduction of speed achieved by the expanded internal diameter of second lumen portion 20 in distal end 14 slows the fluid being delivered to prevent tissue trauma at the fluid ejection site. Thus, the objectives of the present invention are achieved.

Figure 2:
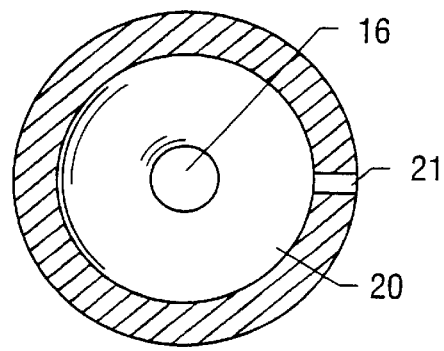
FIG. 2 is an illustration of the microbore catheter shown in FIG. 1, depicted in a cross-sectional view taken along the line A—A in FIG. 1.
Figure 3:
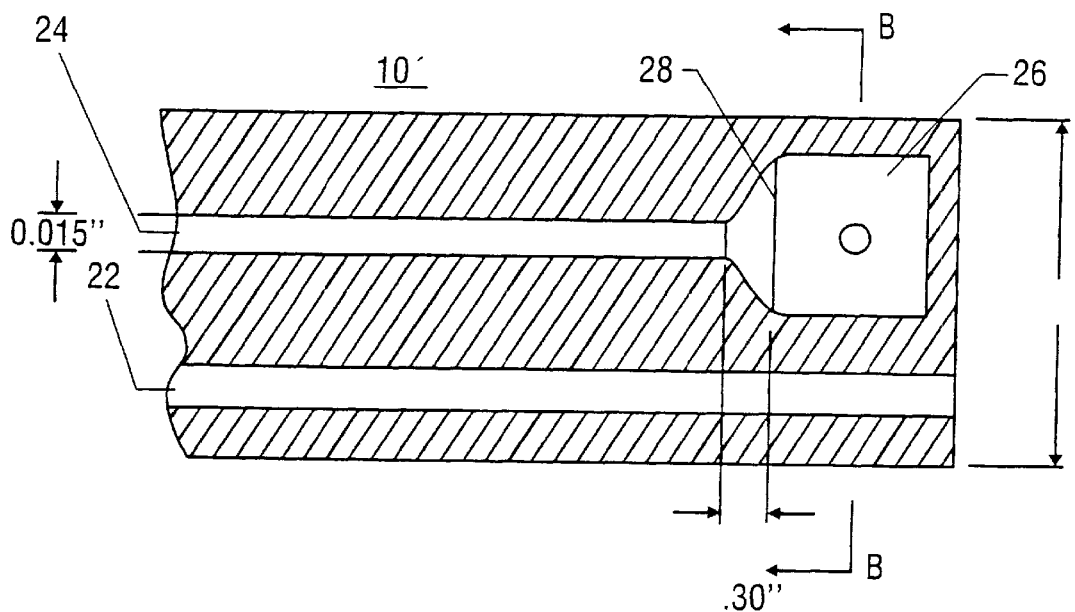
FIG. 3 is an illustration of the microbore catheter according to an additional embodiment of the present invention, having a stylet lumen and a separate fluid delivery lumen, depicted in vertical section.
Figure 4:
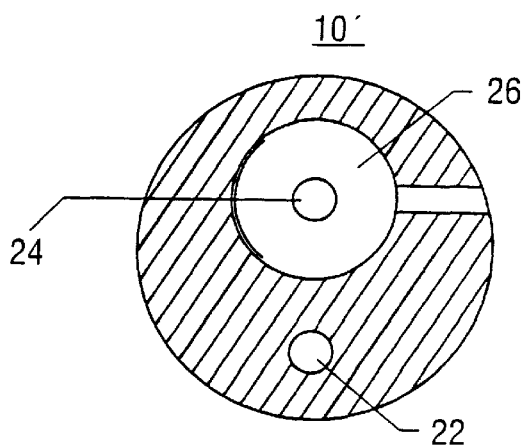
FIG. 4 is an illustration of the present invention as shown in FIG. 3, depicted in a cross-sectional view taken along the line B—B in FIG. 3.

Although, as shown in FIGS. 1 and 2, a microbore catheter may comprise a single lumen for delivery of fluid and for channeling of a stylet or guidewire for use in placement of the catheter at the ejection site, it will be appreciated that alternative structural embodiments incorporating the present invention are possible. For example, as shown in FIGS. 3 and 4, catheter 10' may include a first stylet lumen 22 and a second fluid delivery lumen 24. First stylet lumen 22 is of sufficient size to accommodate a stylet (not shown) for use in extending microbore catheter 10' to the selected location in the patient's body. A typical internal diameter of stylet lumen 22 to accommodate a stylet generally is approximately 0.015–0.030 inches. Stylet lumen 22 may be open or closed at the distal tip of microbore catheter 10' depending upon the requirements of the particular application involved. Second delivery lumen 24 is in general accordance with the embodiment described above with reference to FIGS. 1 and 2, terminating at the distal tip 26 and including a transitional portion 28 for slowing the speed of delivered fluid.

Although the preferred embodiment of this invention has been described hereinabove in some detail, it should be appreciated that a variety of embodiments will be readily available to persons utilizing the invention for a specific end use. The description of the apparatus and method of this invention is not intended to be limiting on this invention, but is merely illustrative of the preferred embodiment of this invention. Other apparatus and methods which incorporate modifications or changes to that which has been described herein are equally included within this application. Additional objects, features and advantages of the present invention will become apparent by referring to the above description of the invention in connection with the accompanying drawings.

What is claimed is:

1. A catheter, comprising:
   a generally elongated tubular member including a first lumen portion having a first inner diameter, a second lumen portion having a second inner diameter greater than said first inner diameter of said first lumen portion, and a transitional lumen portion extending between said first lumen portion and said second lumen portion and having a transitional inner diameter that expands along its length between said first lumen portion and said second lumen portion such that the velocity of the fluid being transported from said first lumen portion toward said second lumen portion will be reduced upon entering said transitional lumen portion, said second lumen portion including a fluid exit opening that is proximate said transitional lumen portion and is substantially open to fluid flow when said second lumen portion is not deformed.

2. A catheter, comprising:

a generally elongated tubular member including a first lumen portion having a first inner diameter, a second lumen portion having a second inner diameter greater than said first inner diameter of said first lumen portion, and a transitional lumen portion extending between said first lumen portion and said second lumen portion and having a transitional inner diameter that expands along its length between said first lumen portion and said second lumen portion such that the velocity of the fluid being transported from said first lumen portion toward said second lumen portion will be reduced upon entering said transitional lumen portion, the length of said transitional lumen portion being approximately 20 times the magnitude of said first inner diameter of said first lumen portion.

3. The catheter assembly of claim 1, wherein the ratio of said second inner diameter of said second lumen portion to said first inner diameter of said first lumen portion is about 3:1.

4. An improved microbore catheter, comprising:

a first lumen for receiving fluid to be delivered to a fluid ejection site within a living body;

a second lumen to be disposed at said fluid ejection site within said living body, said second lumen having an internal diameter greater than an internal diameter of said first lumen; and a transitional lumen extending between said first lumen and said second lumen, said transitional lumen having an internal diameter that expands between the point of connection with said first lumen and the point of connection with said second lumen such that, when fluid is being delivered through said first lumen toward said second lumen, the velocity of said fluid will reduce upon entering said transitional lumen, said second lumen including a fluid exit opening that is proximate said transitional lumen and is substantially open to fluid flow when said second lumen portion is not deformed.

5. An improved microbore catheter, comprising:

a first lumen for receiving fluid to be delivered to a fluid ejection site within a living body;

a second lumen to be disposed at said fluid ejection site within said living body, said second lumen having an internal diameter greater than an internal diameter of said first lumen; and a transitional lumen extending between said first lumen and said second lumen, said transitional lumen having an internal diameter that expands between the point of connection with said first lumen and the point of connection with said second lumen such that, when fluid is being delivered through said first lumen toward said second lumen, the velocity of said fluid will reduce upon entering said transitional lumen, the length of said transitional lumen being approximately 20 times the magnitude of said internal diameter of said first lumen.

6. The microbore catheter of claim 4, wherein the ratio of said internal diameter of said second lumen to said internal diameter of said first lumen is about 3:1.

7. A method of reducing the velocity of fluid being injected within a living body, comprising:

(a) providing a catheter having a first lumen, a second lumen, and a transitional lumen extending in between said first lumen and said second lumen, said second lumen having a greater internal diameter than said first lumen, and said transitional lumen having an internal diameter that expands between said first lumen and said second lumen said second lumen portion including a fluid exit opening that is proximate said transitional lumen portion and is substantially open to fluid flow when said second lumen portion is not deformed;

(b) positioning said second lumen at a predetermined ejection site within a living body; and (c) introducing fluid into said first lumen for delivery toward said second lumen.

8. An apparatus for delivering fluid to an ejection site within a living body, comprising:

a generally tubular member having a first lumen for receiving fluid to be delivered to said ejection site, a second lumen disposed at said ejection site for ejecting said fluid into said living body at said ejection site, and a transitional lumen extending between said first lumen and said second lumen and having an expanding internal diameter between the point of connection with said first lumen and the point of connection with said second lumen such that fluid being delivered from said first lumen toward said second lumen experiences a reduction in velocity upon entering said transitional lumen, said second lumen including a fluid exit opening that is proximate said transitional lumen and is substantially open to fluid flow when said second lumen portion is not deformed.

9. An apparatus for delivering fluid to an ejection site within a living body, comprising:

a generally tubular member having a first lumen for receiving fluid to be delivered to said ejection site, a second lumen disposed at said ejection site for ejecting said fluid into said living body at said ejection site, and a transitional lumen extending between said first lumen and said second lumen and having an expanding internal diameter between the point of connection with said first lumen and the point of connection with said second lumen such that fluid being delivered from said first lumen toward said second lumen experiences a reduction in velocity upon entering said transitional lumen, the length of said transitional lumen being approximately 20 times the magnitude of the internal diameter of said first lumen.

10. The apparatus of claim 8, wherein the ratio of the internal diameter of said second lumen to the internal diameter of said first lumen is about 3:1.

11. A catheter, comprising:

a generally tubular member having a microbore lumen and a velocity reduction chamber, said microbore lumen being for receiving fluid from a fluid supply device to be delivered into said velocity reduction chamber, said velocity reduction chamber being positioned at an ejection site within a living body for delivering said fluid into said living body, said velocity reduction chamber having an internal diameter greater than an internal diameter of said microbore lumen such that said fluid being delivered through said microbore lumen reduces in velocity upon entering said velocity reducing chamber, said velocity reduction chamber including a second lumen having an internal diameter greater than said internal diameter of said microbore lumen, and a transitional lumen extending between said microbore lumen and said second lumen, said transitional lumen having an internal diameter that increases progressively between the point of connection with said microbore lumen and the point of connection with said second lumen, said velocity reduction chamber including a fluid exit opening that is proximate said transitional lumen and is substantially open to fluid flow when said second lumen is not deformed.

12. A catheter, comprising:

a generally tubular member having a microbore lumen and a velocity reduction chamber, said microbore lumen for being receiving fluid from a fluid supply device to be delivered into said velocity reduction chamber, said velocity reduction chamber being positioned at an ejection site within a living body for delivering said fluid into said living body, said velocity reduction chamber having an internal diameter greater than an internal diameter of said microbore lumen such that said fluid being delivered through said microbore lumen reduces in velocity upon entering said velocity reducing chamber, said velocity reduction chamber including a second lumen having an internal diameter greater than said internal diameter of said microbore lumen, and a transitional lumen extending between said microbore lumen and said second lumen, said transitional lumen having an internal diameter that increases progressively between the point of connection with said microbore lumen and the point of connection with said second lumen, the length of said transitional lumen portion being approximately 20 times the magnitude of said internal diameter of said microbore lumen.

13. The catheter of claim 1, wherein the internal diameter of said second lumen portion is substantially the same throughout its length.

14. The catheter of claim 4, wherein the internal diameter of said second lumen is substantially the same throughout its length.

15. The catheter of claim 8, wherein the internal diameter of said second lumen is substantially the same throughout its length.

16. The catheter of claim 11, wherein the internal diameter of said second lumen is the substantially same throughout its length.

17. The catheter of claim 1, wherein the end of said second lumen portion remote from said transitional lumen portion is substantially closed to fluid flow.

18. The catheter of claim 4, wherein the end of said second lumen remote from said transitional lumen is substantially closed to fluid flow.

19. The catheter of claim 8, wherein the end of said second lumen remote from said transitional lumen is substantially closed to fluid flow.

20. The catheter of claim 11, wherein the end of said second lumen remote from said transitional lumen is substantially closed to fluid flow.

21. A catheter, comprising:

a generally elongated tubular member including a first lumen portion having a first inner diameter, a second lumen portion having a second inner diameter greater than said first inner diameter of said first lumen portion, a transitional lumen portion extending between said first lumen portion and said second lumen portion and having a transitional inner diameter that expands along its length between said first lumen portion and said second lumen portion such that the velocity of the fluid being transported from said first lumen portion toward said second lumen portion will be reduced upon entering said transitional lumen portion, and a stylet lumen for accommodating a stylet, said stylet lumen being positioned substantially alongside said first lumen portion, the length of said transitional lumen portion being approximately 20 times the magnitude of said internal diameter of said microbore lumen.

22. The catheter of claim 21, wherein said second lumen portion includes a fluid exit opening.

23. The catheter of claim 22, wherein said transitional lumen portion is proximate said fluid exit opening.

24. The catheter assembly of claim 21, wherein the ratio of said second inner diameter of said second lumen portion to said first inner diameter of said first lumen portion is about 3:1.

* * * * *